United States Patent [19]

Prichep

[11] Patent Number: 5,083,571
[45] Date of Patent: Jan. 28, 1992

[54] USE OF BRAIN ELECTROPHYSIOLOGICAL QUANTITATIVE DATA TO CLASSIFY AND SUBTYPE AN INDIVIDUAL INTO DIAGNOSTIC CATEGORIES BY DISCRIMINANT AND CLUSTER ANALYSIS

[75] Inventor: Leslie S. Prichep, Mamaroneck, N.Y.

[73] Assignee: New York University, New York, N.Y.

[21] Appl. No.: 182,783

[22] Filed: Apr. 18, 1988

[51] Int. Cl.$^5$ .................................... A61N 5/0476
[52] U.S. Cl. .......................................... 128/731
[58] Field of Search ............................ 128/731–732, 128/745

[56] References Cited

U.S. PATENT DOCUMENTS

| | | | |
|---|---|---|---|
| 4,188,956 | 2/1980 | John | 128/731 |
| 4,201,224 | 5/1980 | John | 128/731 |
| 4,275,744 | 6/1981 | Thornton et al. | 128/731 |
| 4,279,258 | 7/1981 | John | 128/731 |
| 4,417,592 | 11/1983 | John | 128/731 |
| 4,493,327 | 1/1985 | Bergelson et al. | 128/731 |

Primary Examiner—William E. Kamm

[57] ABSTRACT

A system for using discriminant analysis of EEG data to automatically evaluate the probability that an individual patient belongs to specified diagnostic categories or a subtype within a category where there are more than two categories or subtypes, and the system automatically places the patient into one of those more than two categories or subtypes.

21 Claims, 11 Drawing Sheets

USE OF BRAIN ELECTROPHYSIOLOGICAL QUANTITATIVE DATA TO CLASSIFY AND SUBTYPE AN INDIVIDUAL INTO DIAGNOSTIC CATEGORIES BY DISCRIMINANT AND CLUSTER ANALYSIS

BACKGROUND AND SUMMARY OF THE INVENTION

The invention is in the field of deriving and using brain electrophysiological data such as EEG (electroencephalographic) and EP (evoked potential) data and focuses on the use of quantitative data of this nature to classify and subtype an individual into one or more diagnostic categories on the basis of the probability of the presence of a specific electro-physiological profile.

It has long been known that time-varying spontaneous electrical potentials (SP) exist between areas of a person's scalp and that an SP record called an electroencephalogram or EEG for short, can be studied in an effort to evaluate brain activity. The EEG data can be presented in analog form, as a set of traces of SP amplitude vs. time from a number of scalp and other electrodes which are electrically referenced in various ways. These traces can be studied visually but the information of interest is difficult to extract accurately because it typically is in the form of low amplitude time-varying signals which tend to be masked by higher amplitude noise and other perturbations. Accordingly, long and specialized training is believed to be required to interpret analog EEG and the process tends to be subjective and time consuming. Another approach is quantitative EEG, which involves digitizing the EEG electrode outputs and subjecting them to sophisticated digital processing in an effort to suppress features which are believed to be less relevant and enhance features which are believed to be more relevant. A great deal of development has taken place in quantitative EEG in recent years as evidenced, for example, by the documents which are cited at the end of this specification and are hereby incorporated by reference in this specification in their entirety as though fully set forth herein. These documents are referred to by citation number in the discussion below. It also has long been known that evoked potential (EP) data can be derived from the same or similar electrodes when the patient is subjected to stimuli such as auditory and visual stimuli. The EP data typically appears as potentials superimposed on the normally present SP signals. See, for example, U.S. Pat. No. 4,493,327, which is hereby incorporated by reference.

A good example of an advanced quantitative EEG instrument is the system which is available under the tradename Spectrum 32 from Cadwell Laboratories, Inc. of Kennewick, Washington. The patents pertaining to such technology include U.S. Pat. Nos. 3,901,215; 4,171,696; 4,188,956; 4,201,224; 4,216,781; 4,279,258; 4,411,273 and 4,417,592, which are hereby incorporated by reference. In a typical operation, the instrument collects EEG data from each of the 19 electrodes of the International 10/20 Placement System. For example, the electrodes are secured to a flexible cap placed over the patient's head. A sufficiently long interval of artifact-free, eyes-closed, resting state EEG is gathered from these electrodes, transmitted to the instrument via a multiconductor cable and recorded therein. The EEG data can be displayed in analog form for a visual check and verification and as an initial indication of the nature of the data. EEG data contaminated by artifacts such as due to muscle or eye movement or environmental noise can be automatically or manually rejected to leave only valid data which are sufficiently free from artifacts to be acceptable for subsequent analysis. For example, EEG data can be collected and screened to extract therefrom 24–48 artifact-free segments each 2.5 seconds long. If the screening is manual, a 2.5 second window can be scanned over the analog display until it encloses only data which appear visually to be artifact-free, the selected segment is marked as acceptable, and the process is repeated until enough good segments have been collected. If the screening is automatic, the artifact-free segments can be selected through the use of artifact-rejection algorithms stored in the instrument.

For quantitative EEG analysis, the EEG analog waveforms typically are converted to digital form so that they can be subjected to various forms of digital processing in order to extract objective descriptors or features of the EEG data and to use such features as a diagnostic aid. For example, Fast Fourier Transform (FFT) analysis is applied to characterize the frequency composition of the EEG data, typically dividing the EEG spectrum into the four traditional frequency bands: delta (1.5–3.5 Hz), theta (3.5–7.5 Hz), alpha (7.5–12.5 Hz) and beta (12.5–20 Hz). These features can include characteristics of the EEG data such as absolute and relative power, symmetry, coherence, etc., for a total of up to hundreds of features. In this context: absolute power is the average amount of power in each frequency band and in the total frequency spectrum of the artifact-free EEG data from each of the 19 electrodes and is a measure of the strength of the brain electrical activity; relative power is the percentage of the total power contributed for a respective electrode and a respective frequency band and is a measure of how brain activity is distributed; symmetry is the ratio of levels of activity between corresponding regions of the two brain hemispheres in each frequency band and is a measure of how balanced is the observed activity; and coherence is the degree of synchronization of electrical events in corresponding regions of the two hemispheres and is a measure of how coordinated is the observed brain activity. These four basic categories of univariate features, resulting from spectral analysis of the EEG data, are believed to characterize independent aspect of brain activity and each is believed to be sensitive to a variety of different clinical conditions and changes of state. In one example, the Spectrum 32 instrument automatically extracts 258 quantitative features representing these four aspects of the EEG spectrum from the monopolar EEG data provided by the 19 electrodes and computes an additional 112 features from 8 bipolar derivations, for a total of 370 features which can be considered univariate measures (i.e., each feature is a measure of the local EEG at one derivation or from the comparison of two derivations). It is believed that the measures of such features should have Gaussian distributions and, if that is not the case, the instrument can transform the appropriate measures into an adequate Gaussian distribution, for example as discussed in John, E. R. et al., The Use of Statistics in Electrophysiology, Handbook of Electroencephalography and Clinical Neurophysiology, Revised Series, Vol. 1, Methods of Analysis of Brain Electrical and Magnetic Signals, edited by Gevins, A. S. et al., Elsevier, 1987, pp. 497–540.

In the case of quantitative EP data, the instrument derives factor Z-scores $Z_{ij}$ from the analog EP data derived from the individual, in the manner discussed below, where the analog output $EP_i(t)$ of the i-th EP electrode is a waveform which is a function of time t and can be approximated by the sum of the typically non-sinusoidal waveforms $F_j(t)$ as follows, where the SUM is from i=1 to i=N (N is the number of EP electrodes, e.g., 19), and from j=1 to j=K (j identifies a particular factor waveform F and K is an integer and is the total number of waveforms F required to achieve a desired accuracy in approximating the waveform $EP_i(t)$), $a_{ij}$ is a coefficient corresponding to the contribution of factor waveform $F_j(t)$ to the approximation of the waveform $EP_i(t)$, and R is a constant:

$$EP_i(t) = SUM[(a_{ij})(F_j(t))] + R$$

The above expression is similar to that for a Fourier series decomposition of a waveform, except that the waveforms $F_j$ need not be and typically are not sinusoidal. In effect, for each EP electrode i the first waveform $F_1(t)$ is derived by least-squares curve fitting the waveform $EP_i(t)$, the second waveform $F_2(t)$ is derived by least-squares curve fitting the difference between waveforms $EP_i(t)$ and $F_1(t)$, etc. until the index K in $F_K(t)$ is high enough for the sum of the waveforms to satisfactorily approximate $EP_i(t)$. Using a historical database of the EP responses to each of a set of standard stimuli of a large population of individuals believed to be normal, the distribution of these responses has been determined for each stimulus and each electrode, i.e., the mean $a_{ij}$ and the standard deviation $sigma_{ij}$ are determined and stored for this large population of normal individuals. The desired factor Z-scores $Z_{ij}$ then are determined in accordance with:

$$EP_i(t) = SUM[(Z_{ij})(F_j(t))] + R$$

where $$Z_{ij} = (a_{ij} - a_{ij})/(sigma_{ij})$$

Similarly derived factor scores $Z_{ij}$ for the SP waveforms can be used in the invented process described below in place of the features discussed in detail, or in combination with such features.

Such features and factor Z-scores can be used to evaluate if and how patients differ from norms which in turn are evaluated from processing similar features derived from large populations of subjects believed to be normal in the relevant context. These norms can be in the form of growth curves representative of the evolution of brain activity with age and are stored in said Spectrum 32 instrument in the form of a database of age regression expressions which define the distribution of every feature of interest as a function of age in a population of subjects believed to be normal. For a patient of a specified age, the instrument extracts from this database the mean value and the standard deviation to be expected for each feature of a group of "normal" subjects the same age as the patient. The instrument automatically evaluates the difference between the value of each feature observed in the patient and the age-appropriate value predicted by the age regression expressions in the database and evaluates the probability that the observed value in the patient would belong to the "normal" group, taking into account the distribution of values in that "normal" group. This process is known as a Z-transformation and yields a Z-score for each feature, derived by dividing the difference between the observed value and the mean of the expected "normal" value by the standard deviation of the expected "normal" value. This process rescales all relevant data into units of probability (or units proportional to probability), yielding a uniform scale in all dimensions which can simplify further comparisons and evaluations of relationships between features.

These Z-scores can then be used to distinguish among different clinical conditions and subgroups within a population through discriminant analysis using discriminant functions comprised of weighted combinations of subsets of variables each of which is believed to contribute to an overall discrimination in some significant way. The distributions of features of two groups of subjects (where the groups are believed to differ in some way, e.g., to belong to different diagnostic categories) can be thought of as two clouds of points in a multidimensional space in which each dimension corresponds to a feature. There may be no significant differences between the two groups in some dimensions (i.e., in some features) but there may be significant differences in other dimensions. An identification problem arises when these clouds of points overlap (i.e., when there is no apparent significant difference between the two groups with respect to some features). as an attempt to define a boundary through the clouds to create a first zone which includes as much as practicable of the first group and as little as possible of the second group and a second zone which includes as much as practicable of the second group and as little as practicable of the first group. A third zone can be defined to encompass an overlap region where it is believed that no reliable classification can be made. In principle, a discriminant function weights the values of selected features for a new individual and adds these weighted values to specify a single point in the relevant multidimensional space. The theory is that this single point then would be in one of the three zones, and the individual would be classified accordingly. See John, E. R. et al., The Use of Statistics in Electrophysiology, Handbook of Electroencephalography and Clinical Neurophysiology, Revised Series, Vol. 1, Methods of Analysis of Brain Electrical and Magnetic Signals, edited by Gevins, A. S. et al., Elsevier, 1987, particularly at pages 534-539.

While the mathematical principles of discriminant analysis have been known for some time and have been used in practice for other purposes, including to classify groups of individuals, it is believed that there has been no prior art approach to make such discriminant analysis practical and sufficiently accurate for classifying an individual into one or more diagnostic category on the basis of the individual's probability of the presence of a specific brain electrophysiological response. It is believed that the prior art techniqus of this nature were focused on finding the difference between groups, which optimizes factors typically different from those which need to be optimized for practical classification of an individual, and that the prior art processes for discriminaiton between groups may not allow a practically accurate classification of an individual. For example, Prichap, L. S., Neurometric Quantitative EEG Features of Depressive Disorders, Cerebral Dynamics, Laterality and Phychopathology, Proc. of Third International Symposium on Cerebral Dynamics, Laterailty and Psychopathology held in Hakone, Japan, Oct.

14–18, 1986, edited by Takahashi, R. et al., Elsevier, 1987, pp. 55–69 discusses at page 59 et seq. the use of prior art discriminant analysis to classify one subgroup of individuals relative to another but does not disclose what particular selection of weighted features could be used in the analysis. It is believed that others have claimed prior art use of discriminant analysis to classify groups of individuals and have used plots of discriminant values in which the values for individuals appear as points on the plot but it is believed that this invention is the first to provide a practical way to classify an individual patient with respect to specified disorders in the manner disclosed below. See, for example, Shagass, C. et al., Phychiatric Diagnostic Discriminations with Combinations of Quantitative EEG Variables, British Journal of Psychiatry (1984), pp. 581–592, and Ford, M. R. et al., EEG Coherence and Power in the Discrimination of Psychiatric Disorders and Medication Effects, BIOL Psychiatry, 1986, 21:1175–1188.

In accordance with a nonlimiting embodiment of the invention, a probabilistic psychiatric classification of an individual patient can be determined using discriminant functions derived from stepwise discriminant analysis of test populations. Each discrimination is based on n functions, where n is equal to the number of groups in that discrimination. The functions are defined as the sum of selected Neuro metric variables, each multiplied by a coefficient. The result of each function is a single discriminant score $s_i$. The result of each function is a single discriminant score $s_i$. A classification probability $P_i$ that an individual belongs to group i is calculated according to the following formula:

$$P_i = \frac{\exp(s_i)}{\sum_{i=1}^{n} \exp(s_i)}$$

The group i for which an individual has the highest probability $P_i$ is selected as a potential classification group.

This probability $P_i$ is then compared to guardband cutoff levels for this group, $a_i, a'_i, a''_i, \ldots$, where $a_i < a'_i < a''_i \ldots$ which correspond to classification errors $\epsilon_i, \epsilon'_i$ and $\epsilon''_i$, where $\epsilon_i < \epsilon'_i < \epsilon''_i$. For example, $\epsilon_i = 10\%$, $\epsilon'_i = 5\%$, and $\epsilon_i\Delta = 2.5\%$.

If $P_i < a_i$ then the individual is not classified. If $a_i \leq P_i < a'_i$ then the individual is classified as group i, with confidence $1 - \epsilon_i$. If $a'_i \leq P_i < a_i\Delta$ then the individual is classified as group i, with confidence $1 - \epsilon'_i$. If $a_i\Delta \leq P_i$ then the individual is classified as group i, with confidence $1 - \epsilon_i\Delta$.

The selection of variables included in the discriminant function and cutoff levels is based on classification curves. FIG. 4 illustrates classification curves for group 1 of a three group discriminant.

Curve $TP_1$ shows the percent of correctly classified individual for the independent replication of group 1 as a function of probability cutoff level. Curves $FP_{21}$ and $FP_{31}$ show percent of incorrectly classified individuals into group 1 from independent replications of group 2 and 3 as functions of probability cutoff levels.

The cutoff level $a_i$ for a given classification error $\epsilon_i$ is selected in such a way that the maximum percent of FP across all other groups is equal to $\epsilon_i$. The additional levels $a'_i$ and $a\Delta_i$ are selected in the same way.

The sensitivity of classification for the group is estimated based on curve $TP_1$.

Analogous classification curves are constructed for all groups in the discriminant.

The variables for the discriminant function are selected to provide optimal sensitivity for all groups for the desirable level of classifications errors. These levels can be different for different groups.

In practice, the invention can be embodied in an instrument such as said Spectrum 32 instrument and can be used interactively by the instrument operator to evaluate a patient. For example, the operator can ascertain from clinical observation and from questioning the patient if there are factors which might make the discriminant analysis, or some aspect of it, less reliable and can modify of discontinue the discriminant analysis accordingly. For example, certain medication can normalize an otherwise abnormal profile while other medication can introduce drug-related abnormal features. For such cases the invented system permits the operator to bypass some or all of the automated patient classification steps or to manually force classification into a selected category.

DETAILED DESCRIPTION

Figure 1:
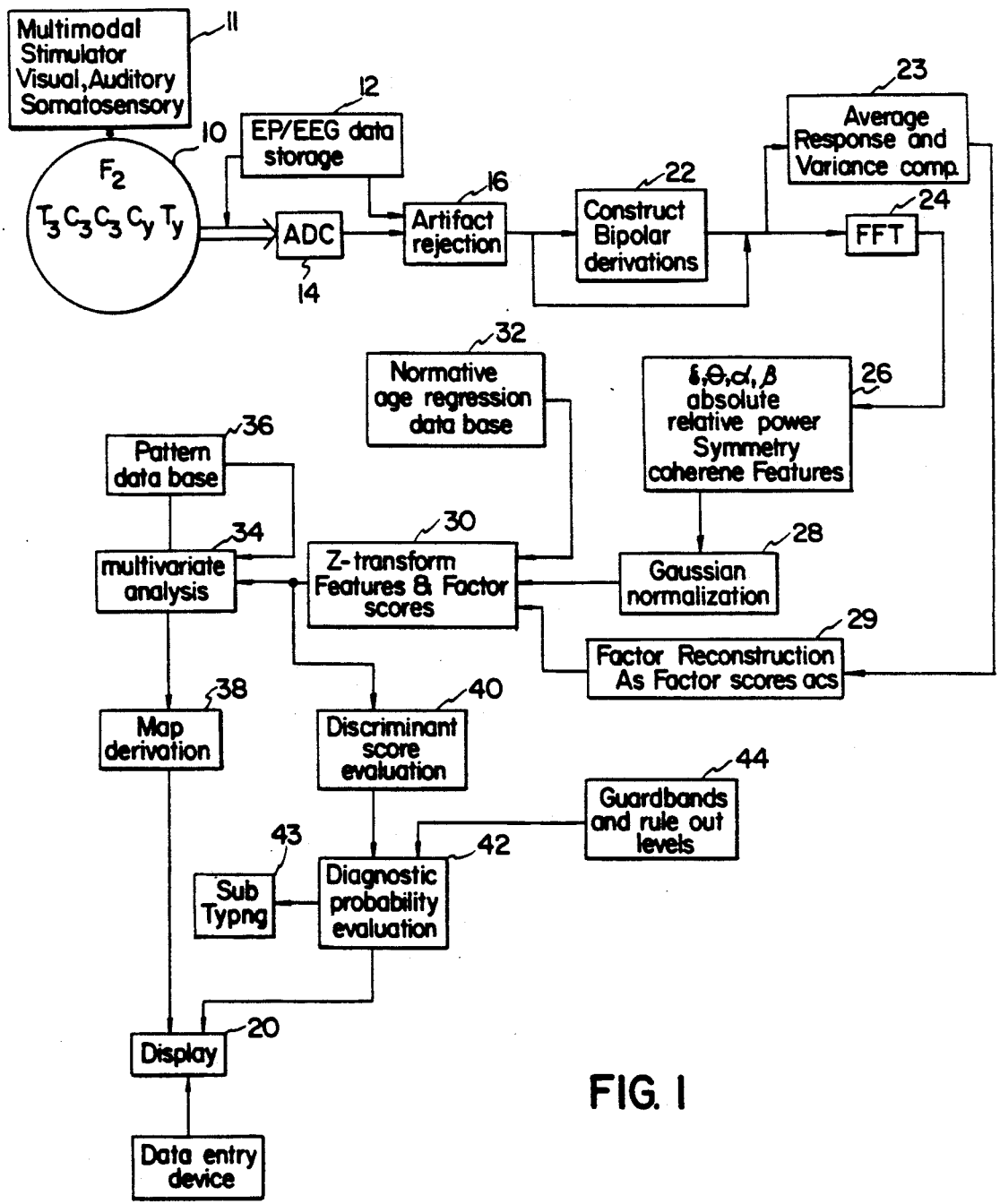
FIG. 1 is a block diagram illustrating an embodiment of the invented system.

Referring to FIG. 1, which illustrates as much of the structure of said Spectrum 32 EEG instrument as is needed to interact with this invention, EEG measurements are derived from electrodes such as T3, C3, Cz, C4, etc., which can be placed on the head 10 of a patient in a configuration such as the International 10/20 Placement System. For EP data, a multimodal stimulator 11 generates appropriate stimuli and the same set of electrodes can be used to derive the analog EP signals. In the alternative, previously derived EEG or EP measurements or digitized EEG or EP data, either with or without prior preprocessing, can be derived from a storage device 12, which can be a memory device such as an optical disc drive or a magnetic disc drive. The analog EEG or EP measurements from the respective electrodes may be amplified and filtered as desired by analog circuits which are not shown, and are converted to digital form at an analog-to-digital converter 12 to enable the instrument to apply further processing by digital techniques. Artifact rejection is applied at unit 16 which can implement a known artifact rejection algorithm and/or can be manually controlled through a data entry device 18 which can comprise a keyboard and an implement such as a trackball or a mouse and is connected to a display 20 which can comprise a CRT display and/or a hard copy output device such as a printer or plotter. While for simplicity FIG. 1 omits some of the connections of data entry device 18 and display 20 with the other illustrated units, it should be clear that such connections exist to the extent needed to carry out the functions discussed below. For manual artifact rejection, or for manual acceptance or rejection or modification of the automatic artifact rejection at unit 16, the waveforms from some or all electrodes can be displayed at display 20 and the operator through data entry device 18 can bracket and mark as accepted or rejected selected portions of the displayed waveforms. If enough data segments of sufficient time durations remain after the artifact rejection processing at unit 16, e.g., 24-48 segments each 2.5 seconds long, the accepted segments can be processed at unit 22 to derive any bipolar measurements that may be desired (for unipolar measurements unit 22 can be bypassed). Typically, 19 monopolar and 8 bipolar measurements are used. These measurements are subjected to Fast Fourier Transform spectral analysis at FFT unit 24 to characterize the frequency content of the EEG measurement segments, typically in the four traditional frequency band known as the delta, theta, alpha and beta bands. Unit 26 then derives four basic categories of univariate features from the results of this spectral analysis processing for each of the four traditional frequency bands and for the total frequency spectrum of the EEG measurements for each of the monopolar signals from 19 electrodes and each of the 8 bipolar signals derived by unit 22. These four basic categories are (1) the absolute power, which is a measure of how strong is the brain activity; (2) the relative power, which is a measure of how the brain activity is distributed among the frequencies of identified monopolar and bipolar measurements; (3) the symmetry, which is a measure of how balanced is the brain activity; and (4) the coherence, which is a measure of how coordinated is the brain activity of the patient. The resulting set of univariate features is subjected to Gaussian normalization at unit 28 in order to improve the accuracy of subsequent statistical analysis At this stage, the features are in respective units such as units of power or units of ratios or percentages, and therefore cannot be conveniently combined with each other for multivariate analysis For EP data, unit 23 derives the average response and variance components of the data and supplies the result to a unit 29 which computes the factor scores $a_{ij}$ discussed above, based on stored normative data. In order to conform the signals from units 28 and 29 to the same unit system, they are subjected at unit 30 to Z-transform processing in which they are converted to units of probability. In particular, each observed feature or factor score is converted to a Z-transform score or a factor Z-score which characterizes the probability that the feature value or factor score observed in the patient will conform to the value for a "normal" individual, taking into account the dispersion of values for this feature or factor score in a "normal" population. The evaluation of the Z-transform score uses normative age regression information from a database stored in unit 32, and can be expressed as subtracting the mean of the "normal" value from the observed value and dividing the result by the standard deviation of the "normal" value, where the mean and the standard deviation are supplied from the database in unit 32. These univariate Z-scores derived at unit 30 can now be used conveniently and effectively in multivariate analysis because they are in the same units of probability and are already age-corrected. The Spectrum 32 instrument can carry out such multivariate analysis in unit 34 by combining univariate Z-scores from unit 30 with each other in selected patterns, taking into account their deviations from normal covariance to compute the multivariate feature called Mahalanobis distance, which can be analogously evaluated by Z-transform relative to a normative database. The resulting Z-score patterns with corresponding patterns from a pattern database 36 to thereby evaluate the probability that patterns derived from the individual patient correspond to the patterns for a "normal" subject. This quantitative evaluation can involve relationships among different features within a local derivation (for example the degree of abnormality of the frequency spectrum across all bands for a selected electrode), or relationships of a feature or a group of features among regional sets of derivations (for example, the pattern of coherence for the entire frequency spectrum between the two hemispheres; or the overall pattern of frequency distribution, coherence and symmetry of the total EEG record). Maps can then be derived at unit 38 and displayed at display 20 to illustrate various characteristics of brain function.

Referring now to the change in said instrument due to the invention, the Z-scores derived by unit 30 for the features of interest are supplied to unit 40 for the evaluation of selected discriminant scores. Each discriminant score is a respective weighted combination of a selected subset of Z-scores for monopolar and/or bipolar univariate and multivariate features derived from the EEG or EP data of an individual patient For example, unit 40 evaluates a respective discriminant score for each of these two or more diagnostic categories multiplying each of several selected Z-scores by a respective coefficient and adding the resulting products. The coefficients typically differ as between diagnostic categories and as between Z-scores A discriminant score therefore is in age-corrected units of probability, as are its constituent Z-scores Unit 42 then evaluates the probability that the individual belongs to one of the two or more diagnostic categories through a probability-evaluating expression which is a function of the relevant discriminant scores, matching the results against guardbands provided by unit 44 to improve classification reliability. Further subtyping within a category can be carried out in unit 43. The resulting classification probability is displayed and/or recorded at 20, and the process is repeated for the desired number of classifications. For example, in order to evaluate the probability that an individual is in the category of normal patients vs. patient having primary depression, the expression used to evaluate the discriminant score DS is:

$$DS = A_1F_1 + A_2F_2 + A_3F_3 + A_4F_4 + A_5F_5 + A_6F_6 \; FC$$

where $A_1-A_6$ are coefficients for the respective features $F_1-F_6$, which can be Z-scores based on monopolar or bipolar derivations, and/or univariate and multivariate features, and FC is a function constant. The constants $A_1-A_6$ and the variables $F_1-F_6$ are as shown in Table 1 below in this example of evaluating the discriminant scores DS for the normal and primary (depression) categories:

TABLE 1

| NORMAL vs PRIMARY DEPRESSION | | | |
|---|---|---|---|
| VARIABLE | NORMAL | PRIMARY | |
| $F_1$ Left Fronto/Temporal Bipolar Absolute Power | −0.03746 | 0.75010 | $A_1$ |
| $F_2$ Parietal Delta Bipolar Coherence | −0.02351 | −0.50883 | $A_2$ |
| $F_3$ Anterior Bipolar Coherence | −0.05034 | 1.05778 | $A_3$ |
| $F_4$ Central Bipolar Asymmetry | −0.02733 | 0.55487 | $A_4$ |
| $F_5$ Anterior Bipolar Asymmetry | −0.02111 | 0.81269 | $A_5$ |
| $F_6$ Anterior Beta Monopolar Relative Power | −0.10229 | 0.39695 | $A_6$ |
| Function Constant | −0.70165 | −2.89319 | FC |

The guardbands for this case are:

| GUARDBANDS | a | a' | a'' |
|---|---|---|---|
| Normal | 65 | 75 | 85 |
| Primary | 60 | 72 | 90 |

Figure 2A:
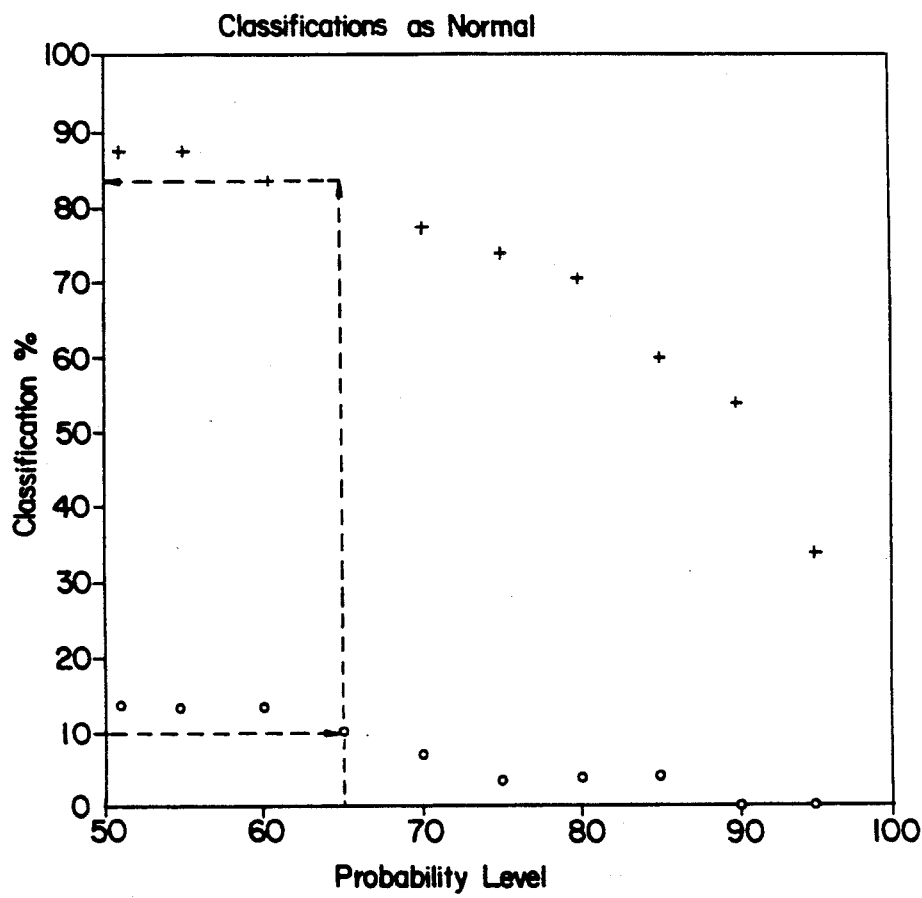
FIGS. 2a and 2b are plots illustrating the classification of an individual in the diagnostic categories of normal and primary depression based on probability levels derived from discriminant functions which in turn are derived as weighted combinations of features extracted from quantitative EEG data.
Figure 2B:
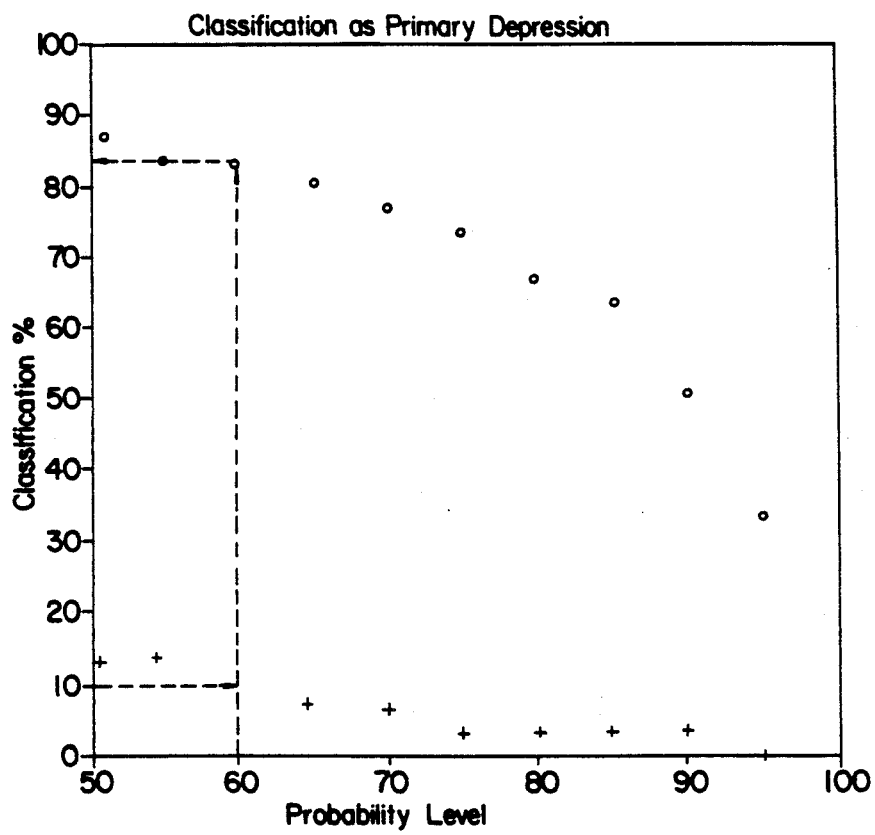

Table 1 above also sets forth the guardbands for the relevant diagnostic categories. The significance of these guardbands is illustrated in FIGS. 2a and 2b. In these plots, the horizontal axis is in units of evaluated probability that the individual belongs to the respective diagnostic category (normal for 2a and primary depression for 2b) and the vertical axis is in units of the percentage of the individuals correctly classified in the respective diagnostic category. The symbol + in each case designates correctly classified individuals (normal individuals correctly classified as normal in 2a, and primary depression individuals correctly classified in the primary depression category in 2b), and the small circle symbol designates incorrectly classified individuals (primary depression individuals incorrectly classified as normal in 2a, and normal individuals incorrectly classified in the primary depression category in 2b). In each of FIGS. 2a and 2b the vertical dash line represents the lowest guardband (evaluated probability levels which are below this guardband are considered too unreliable for diagnostic classification). Thus, if the guardband in FIG. 2a is set at 65 (i.e., 65%), only probabilities of 65 or more would be accepted for the proposition that the individual belongs to the normal rather than the primary depression category. All case of lower probability would not considered reliable enough. Then, 81.4% of the normal individuals would be correctly classified as normal and 10% of the primary depression individuals would be incorrectly classified as normal. The remaining 8.6 of the individuals would remain unclassified. If the guardband is set at 75, 73.4% of the normal individuals would be correctly classified as normal, 4.5% of the primary depression individuals would be incorrectly classified as normal and 22.1% of the individuals would remain unclassified. If the guardband is set at 85, 61.4% of the normal individuals would be correctly classified as normal, 2.3% of the primary depression individuals would be incorrectly classified as normal and 34.3% of the individuals would remain unclassified.

FIG. 2b similarly illustrates the significance of the guardbands with respect to the evaluated probability that an individual is in the primary depression rather than the normal category. Again it is seen that an accuracy of over 80% true positives and 10% or less of false positives (at less than 10% unclassified individuals) is achieved at the lowest level guardband in this example of the invention.

Figure 5:
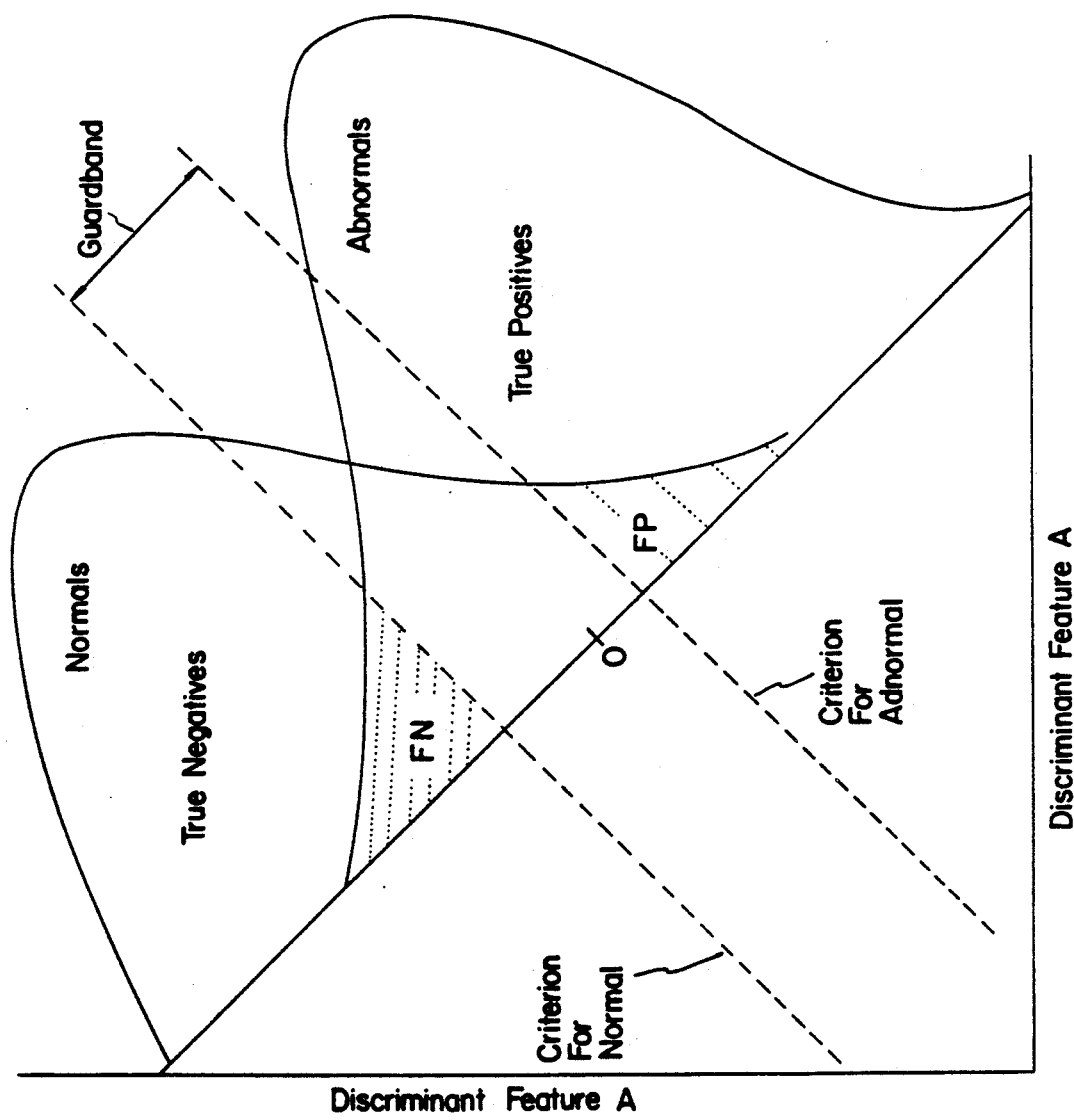
FIG. 5 illustrates a guardband for a classification based on discriminant features A and B.
Figure 6:
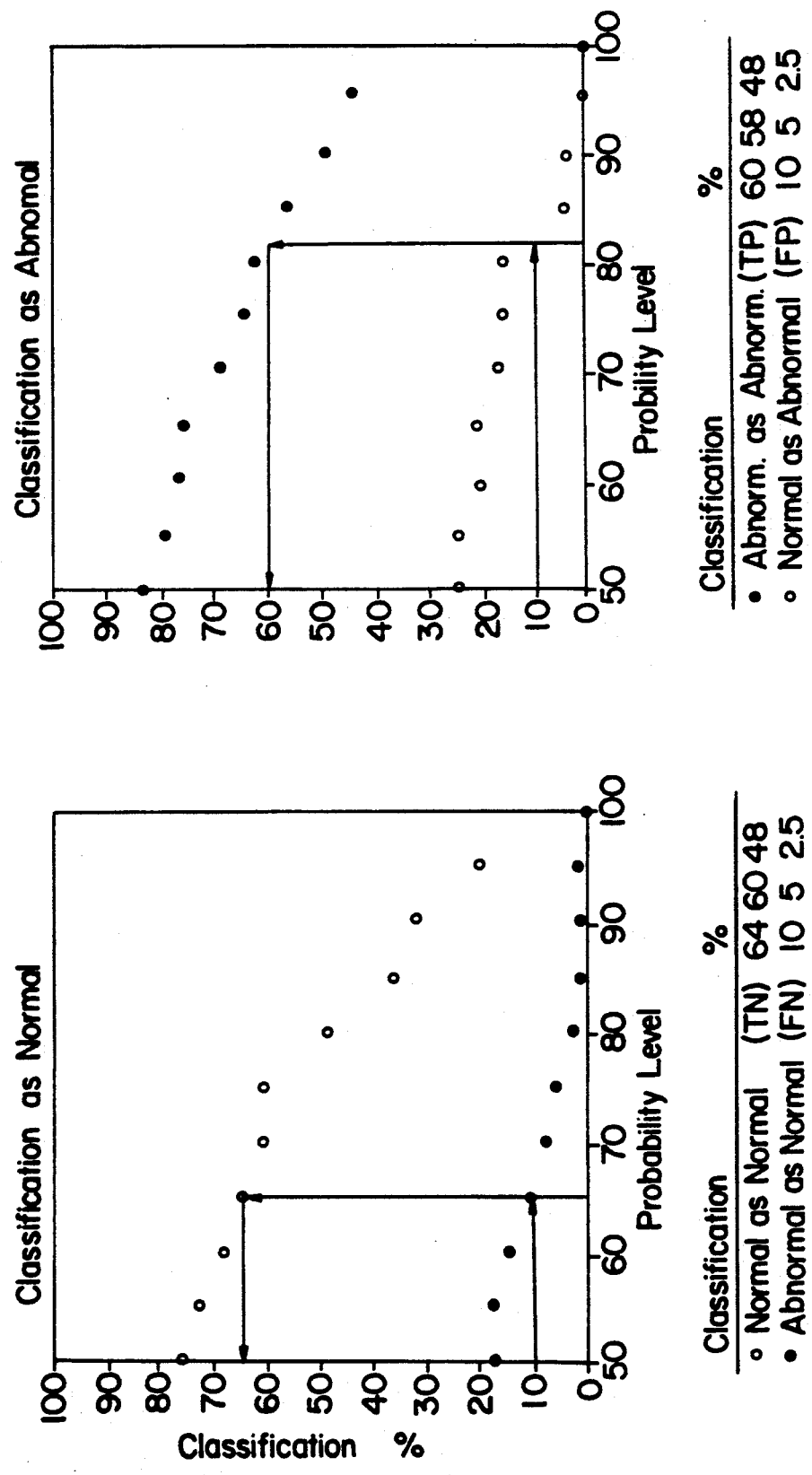
FIG. 6 illustrates the classification of normal versus abnormal adults and corresponds to table 2.
Figure 7:
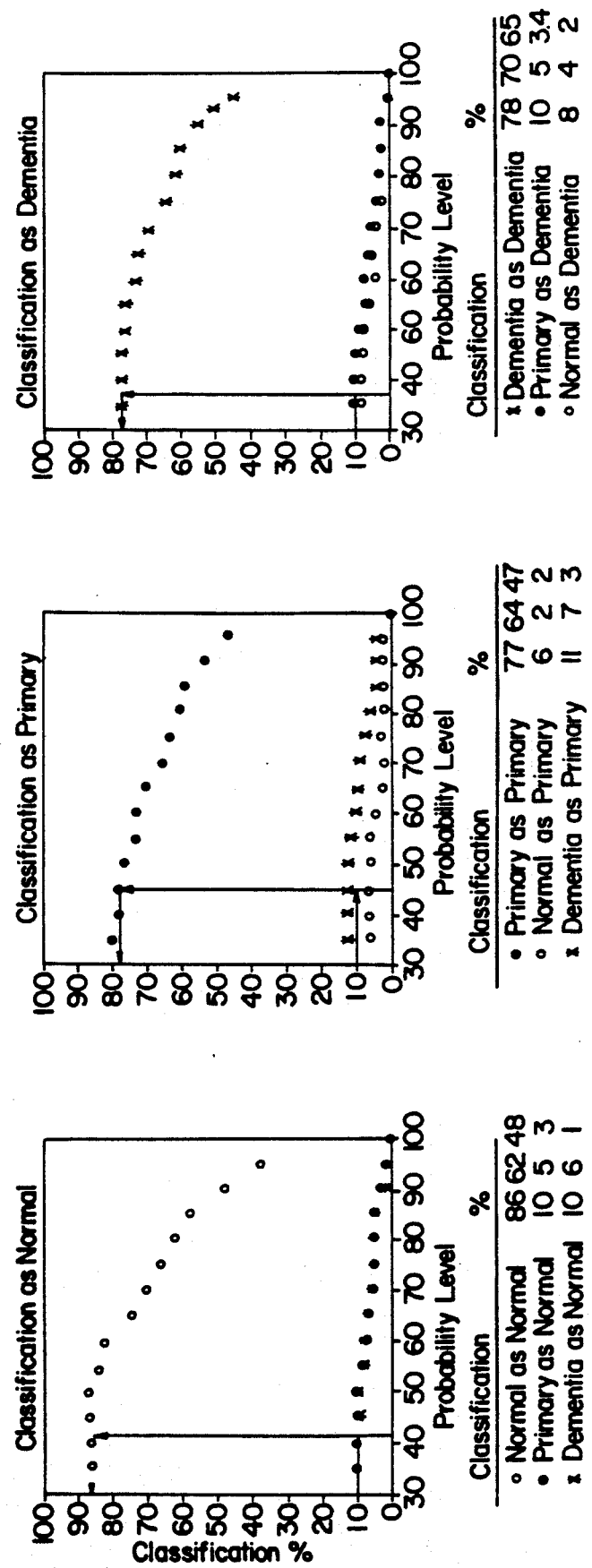
FIG. 7 comprises classification plots corresponding to table 4.
Figure 8:
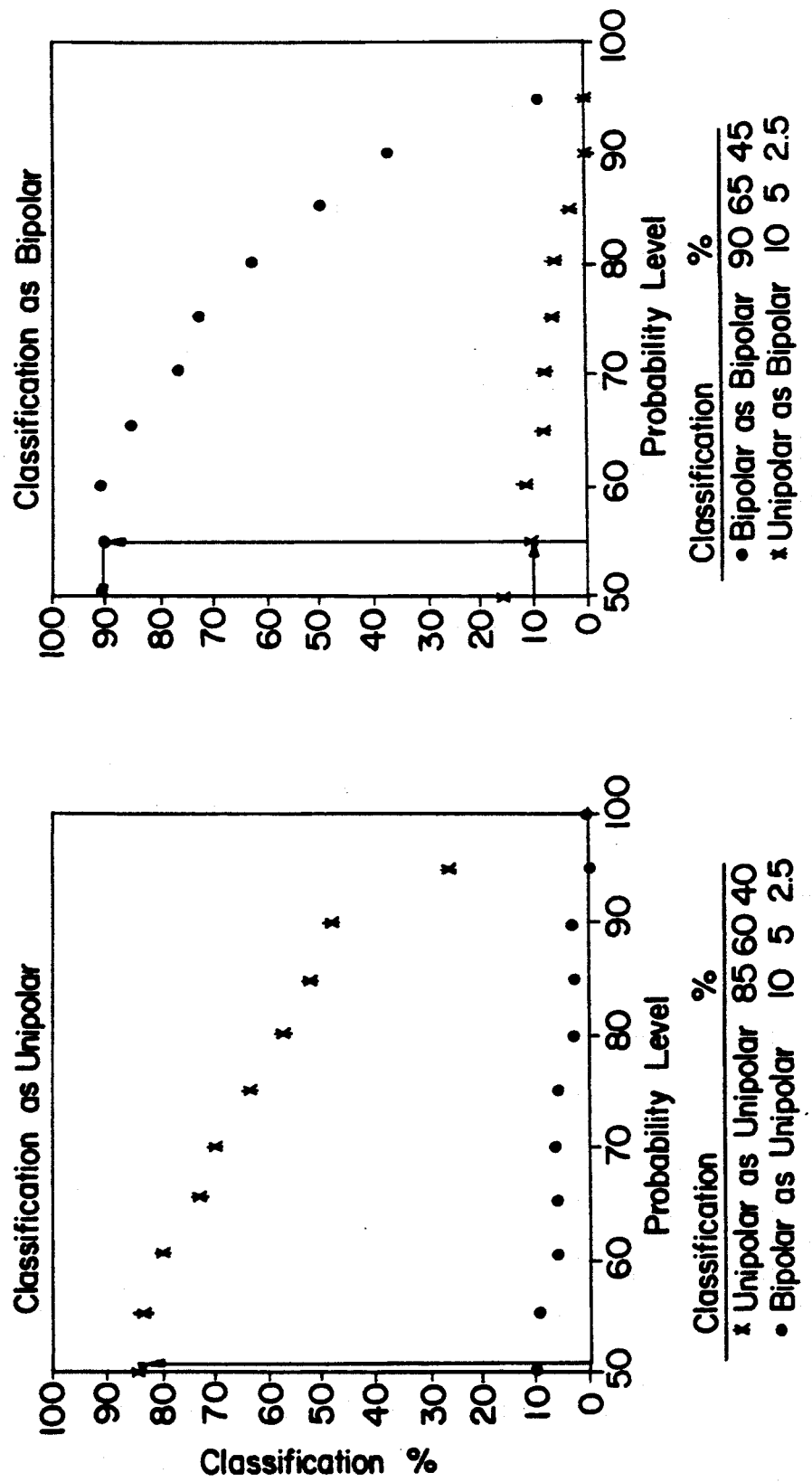
FIG. 8 comprises classification plots corresponding to table 5.
Figure 9:
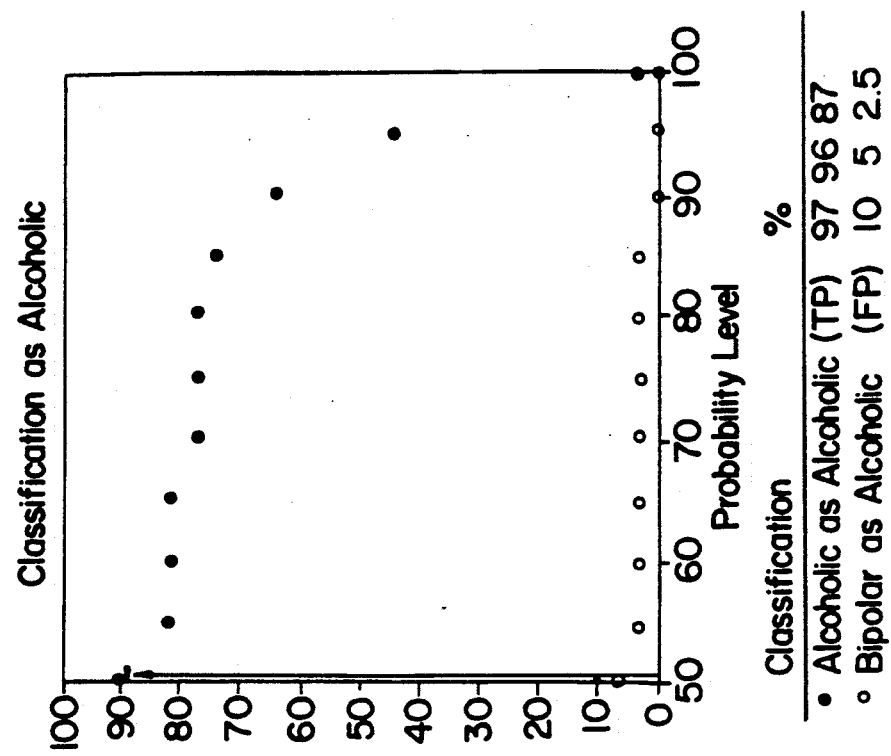
FIG. 9 comprises classification plots corresponding to table 7.
Figure 9:
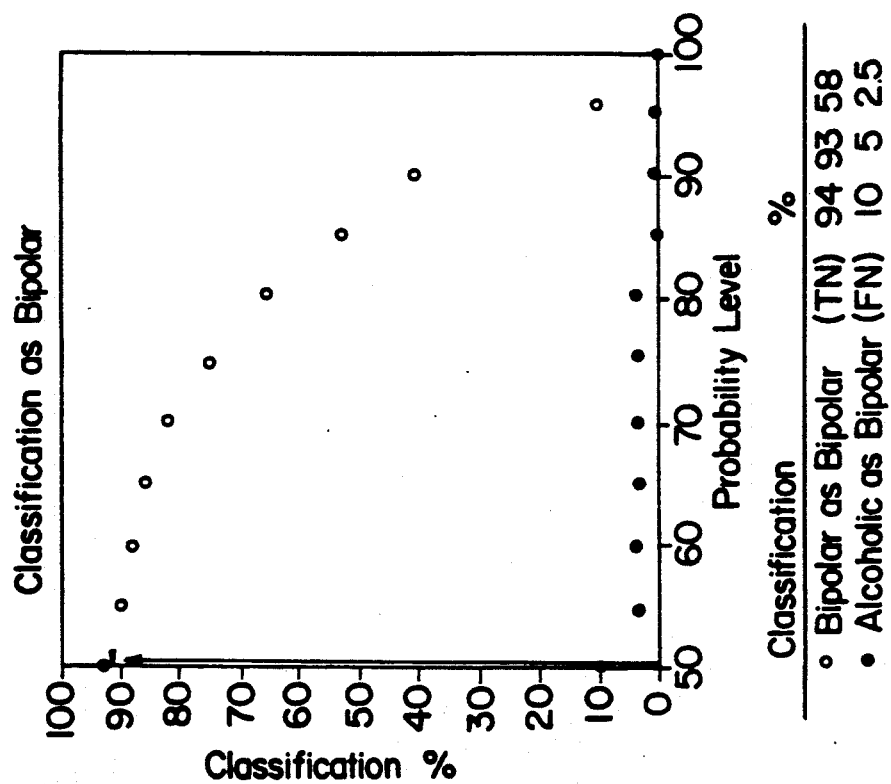
Figure 10:
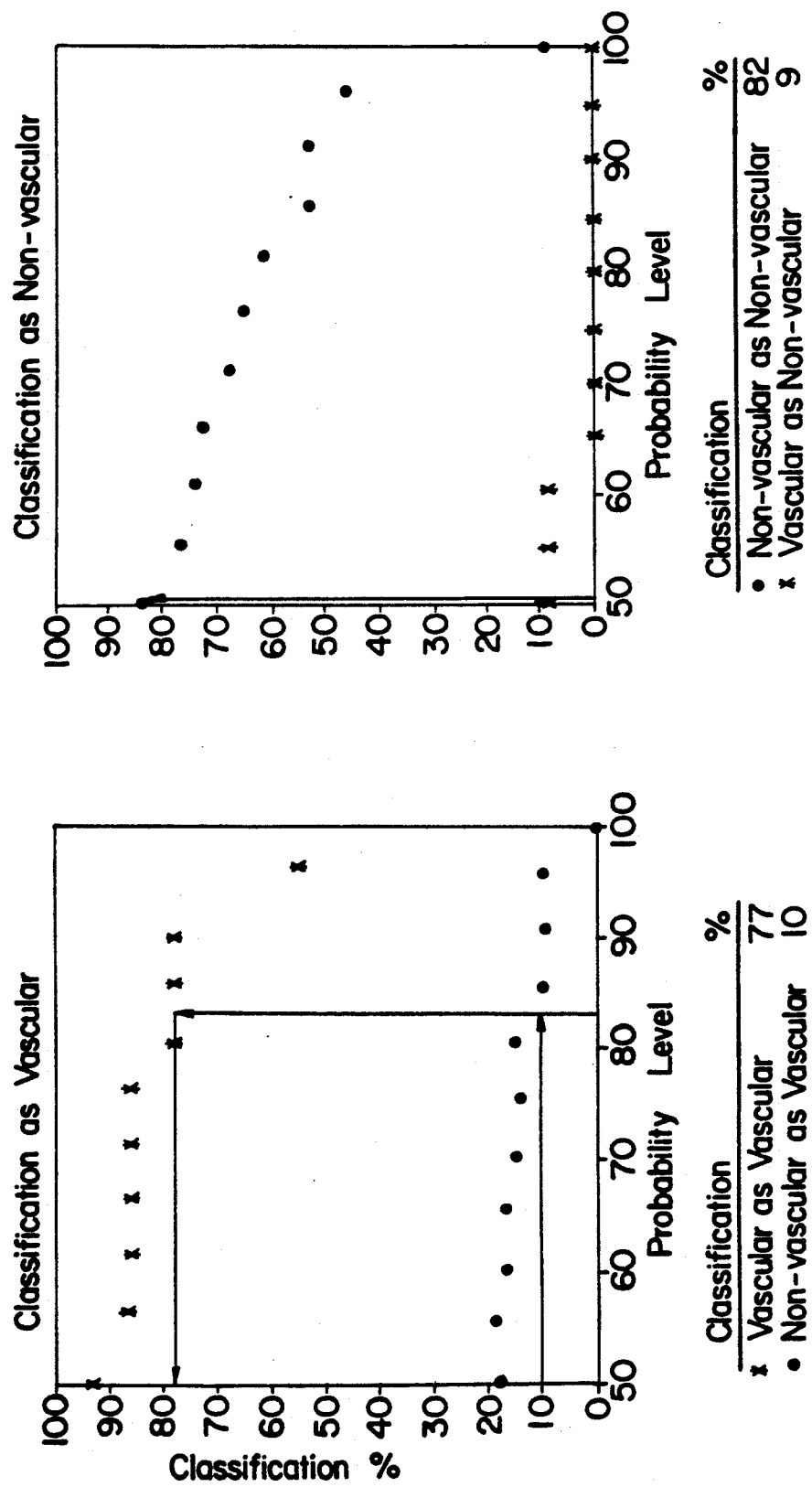
FIG. 10 comprises classification plots for the categories of vascular versus non-vascular dementia.

The significance of guardbands is illustrated in FIG. 5 in a plot for an exemplary classification based on two discriminant functions.

The tables below set forth in a similar manner the coefficients and the features found to be useful in classifying an individual in a diagnostic category in accordance with respective examples of the invention. In each case, the general expression for computing the discriminant score DS is:

$$DS = A_1F_1 + A_2F_2 + \ldots + A_NF_N FC$$

where N equals the number of features and/or factor Z-scores used in the computation of the respective discriminant score. In each of the following Tables, the features and/or factor Z-scores are identified by the work description conventionally used in the art and in particular in connection with said Spectrum 32 instrument. The above expression is computed once for the coefficients A listed under the heading NORMAL and once for the coefficients A listed under the heading ABNORMAL or the appropriate heading of a disorder such as PRIMARY DEPRESSION of DEMENTIA.

TABLE 2

| NORMAL vs ABNORMAL for AGE GREATER THAN 50 YEARS | | |
|---|---|---|
| VARIABLE | NORMAL | ABNORMAL |
| All Regions Delta Bipolar Relative Power | 0.00000 | 0.00000 |
| All Regions Theta Bipolar Relative Power | −0.02961 | 0.36594 |
| All Regions Alpha Bipolar Relative Power | 0.05106 | −0.25480 |
| All Regions Beta Bipolar Relative Power | 0.03480 | 0.31069 |
| Anterior All Frequencies Bipolar Coherence | −0.02934 | 0.59480 |
| Posterior All Frequencies Bipolar Coherence | −0.00501 | 0.32559 |
| Anterior All Frequencies Bipolar Asymmetry | −0.01403 | 0.44775 |
| Posterior All Frequencies Bipolar Asymmetry | −0.02759 | 0.36308 |
| Anterior Combined Frequencies Monopolar Absolute Power | −0.05146 | 0.61554 |
| Posterior Combined Frequencies Monopolar Absolute Power | 0.00000 | 0.00000 |
| Function Constant | −0.69861 | −2.23015 |

| GUARDBANDS | a | a' | a'' |
|---|---|---|---|
| Normal | 65 | 75 | 80 |
| Abnormal | 80 | 85 | 90 |

TABLE 3

| NORMAL vs ABNORMAL for AGE LESS THAN OR EQUAL TO 50 YEARS | | |
|---|---|---|
| VARIABLE | NORMAL | ABNORMAL |
| All Regions Delta Bipolar Relative Power | 0.00000 | 0.00000 |
| All Regions Theta Bipolar Relative Power | 0.00000 | 0.00000 |
| All Regions Alpha Bipolar Relative Power | 0.04777 | −0.48710 |
| All Regions Beta Bipolar Relative Power | 0.02004 | 0.46486 |
| Anterior All Frequencies Bipolar Coherence | −0.02881 | 0.75448 |
| Posterior All Frequencies Bipolar Coherence | −0.00612 | 0.30889 |
| Anterior All Frequencies Bipolar Asymmetry | −0.01651 | 0.48136 |

TABLE 3-continued

NORMAL vs ABNORMAL for AGE LESS THAN OR EQUAL TO 50 YEARS

| | | |
|---|---|---|
| Posterior All Frequencies Bipolar Asymmetry | −0.02686 | 0.38016 |
| Anterior Combined Frequencies Monopolar Absolute Power | −0.05588 | 0.53385 |
| Posterior Combined Frequencies Monopolar Absolute Power | 0.00000 | 0.00000 |
| Function Constant | −0.69794 | −2.08874 |

| GUARDBANDS | a | a' | a" |
|---|---|---|---|
| Normal | 65 | 75 | 85 |
| Abnormal | 65 | 75 | 80 |

TABLE 4

NORMAL vs PRIMARY DEPRESSION vs DEMENTIA

| VARIABLE | NORMAL | PRIMARY | DEMENTIA |
|---|---|---|---|
| All Regions Theta Bipolar Relative Power | −0.02079 | 0.17234 | 1.30229 |
| Left Fronto/Temporal Bipolar Absolute Power | −0.04421 | 1.02014 | 0.04645 |
| Parietal Delta Bipolar Coherence | −0.00752 | −0.74484 | −0.27939 |
| Fronto/Temporal Delta Bipolar Coherence | −0.00899 | −0.53506 | 0.52687 |
| Anterior Bipolar Coherence | −0.04753 | 0.77702 | 0.94400 |
| Central Bipolar Asymmetry | −0.03740 | 0.57220 | 0.62493 |
| Anterior Bipolar Asymmetry | −0.01438 | 0.64457 | 0.43654 |
| Cz Theta Monopolar Relative Power | −0.00180 | −0.79164 | 1.09048 |
| P3 Alpha Monopolar Relative Power | −0.24440 | 2.82880 | 1.73974 |
| O1 Alpha Monopolar Relative Power | 0.27980 | −4.06245 | −1.92960 |
| Anterior Beta Monopolar Relative Power | −0.08958 | 0.35577 | 0.59821 |
| Function Constant | −1.11186 | −4.39809 | −4.63901 |

| GUARDBANDS | a | a' | a" |
|---|---|---|---|
| Normal | 42 | 80 | 90 |
| Primary | 40 | 70 | 75 |
| Dementia | 45 | 75 | 95 |

TABLE 5

UNIPOLAR vs BIPOLAR DEPRESSION

| VARIABLE | UNIPOLAR | BIPOLAR |
|---|---|---|
| Right Temporal Beta Bipolar Relative Power | −0.91564 | 1.26876 |
| Left Lateral Alpha Monopolar Relative Power | −0.15510 | 1.53144 |
| O1 Delta Monopolar Asymmetry | −0.13401 | 0.13963 |
| Right Temporal Alpha Bipolar Relative Power | −0.72519 | 1.57794 |
| Left Temporal Alpha Bipolar Relative Power | −0.06270 | −1.59622 |
| Beta C3 Monopolar Relative Power | 0.04106 | −1.97474 |
| Beta Cz Monopolar Relative Power | 0.26946 | 1.57156 |
| Fronto-temporal Bipolar Absolute Power Asymmetry | 0.01198 | −0.75104 |
| Function Constant | −0.89218 | −2.09228 |

| GUARDBANDS | a | a' | a" |
|---|---|---|---|
| Unipolar | 50 | 77 | 92 |
| Bipolar | 55 | 82 | 87 |

TABLE 6

PRIMARY DEPRESSION vs ALCOHOL ABUSE

| VARIABLE | PRIMARY | ALCOHOLC |
|---|---|---|
| Left Central Beta Bipolar Relative Power | −0.07380 | 0.58635 |
| Left Fronto/Temporal Beta Bipolar Relative Power | −0.08163 | 0.58543 |
| Right Fronto/Temporal Bipolar Absolute Power | 0.76931 | −0.20846 |
| Fronto/Temporal Delta Bipolar Coherence | −0.80124 | −0.05935 |
| Fronto/Temporal Beta Bipolar Coherence | −0.26573 | 0.60565 |
| Posterior Beta Bipolar Asymmetry | 0.45822 | −0.59687 |
| Fz Theta Monopolar Relative Power | −0.07747 | −0.96582 |
| Constant | −1.79117 | −2.61208 |

RULE-OUT LEVEL:

| | |
|---|---|
| Alcoholic | 65 (if $P_i \geq 65\%$, rule out alcoholism) |

TABLE 7

BIPOLAR DEPRESSION vs ALCOHOL ABUSE

| VARIABLE | BIPOLAR | ALCOHOLC |
|---|---|---|
| Right Parietal/Occipital Beta Bipolar Relative Power | 0.58452 | 0.08115 |
| Parietal/Occipital Delta Bipolar Coherence | −0.72523 | −0.20808 |
| Fronto/Temporal Delta Bipolar Coherence | −0.95221 | 0.20967 |
| Parietal/Occipital Beta Bipolar Coherence | −0.01620 | 0.45588 |
| Posterior Bipolar Asymmetry | 0.65121 | −0.80888 |
| Posterior Alpha Monopolar Relative Power | 0.83039 | −0.51708 |
| Fz Theta Monopolar Absolute Power | 1.02508 | −1.29232 |
| Constant | −2.16285 | −1.88824 |

RULE-OUT LEVEL:

| | |
|---|---|
| Alcoholic | 51 |

TABLE 8

ELDERLY DEMENTIA vs ALCOHOL ABUSE

| VARIABLE | DEMENTIA | ALCOHOLC |
|---|---|---|
| Left Central Theta Bipolar Relative Power | −0.03469 | 0.91110 |
| Right Central Theta Bipolar Relative Power | 1.06487 | −1.18625 |
| Left Central Beta Bipolar Relative Power | 0.03015 | 0.89450 |
| Parietal/Occipital Beta | −0.08565 | 0.89726 |

TABLE 8-continued

| ELDERLY DEMENTIA vs ALCOHOL ABUSE | | |
|---|---|---|
| Bipolar Coherence C3–C4 Theta | −0.40997 | 0.09382 |
| Monopolar Asymmetry Constant | −1.82594 | −1.98809 |
| RULE-OUT LEVEL: | | |
| Alcoholic | 51 | |

TABLE 9

| UNIPOLAR DEPRESSION vs ALCOHOL ABUSE | | |
|---|---|---|
| VARIABLE | UNIPOLAR | ALCOHOLC |
| Left Central Beta Bipolar Relative Power | −0.12390 | 0.86921 |
| Left Fronto/Temporal Beta Bipolar Relative Power | −0.31110 | 0.86605 |
| Fronto/Temporal Delta Bipolar Coherence | −0.59866 | −0.14523 |
| Left Central Bipolar Absolute Power | 0.88585 | −0.14734 |
| Parietal/Occipital Beta Bipolar Coherence | 0.00458 | 0.90921 |
| Posterior Bipolar Asymmetry | 0.50132 | −0.57529 |
| Constant | −1.71888 | −2.47368 |
| RULE-OUT LEVEL: | | |
| Alcoholic | 51 | |

TABLE 10

| Learning Disabilities | Normal | LearnDis |
|---|---|---|
| Posterior Combined Measures Bipolar | 0.00343 | 0.52430 |
| All Regions Beta Asymmetry Bipolar | 0.17642 | −0.30199 |
| Pz Alpha Monopolar Relative Power | −0.12530 | 0.72627 |
| Combined Head Monopolar Coherence | −0.00357 | 0.27760 |
| F3F4 Theta Monopolar Coherence | 0.06347 | −0.20188 |
| Total F3F4 Monopolar Asymmetry | −0.00443 | −0.49412 |
| Sum of 8 Bipolar Univariate Alpha Relative Power | −0.00789 | −0.05715 |
| Pz Alpha Monopolar Absolute Power | 0.15789 | −0.76485 |
| Constant | −0.72469 | −1.80925 |
| Guardband: | | |
| Learning Disabled | 73 | |

Figure 3:
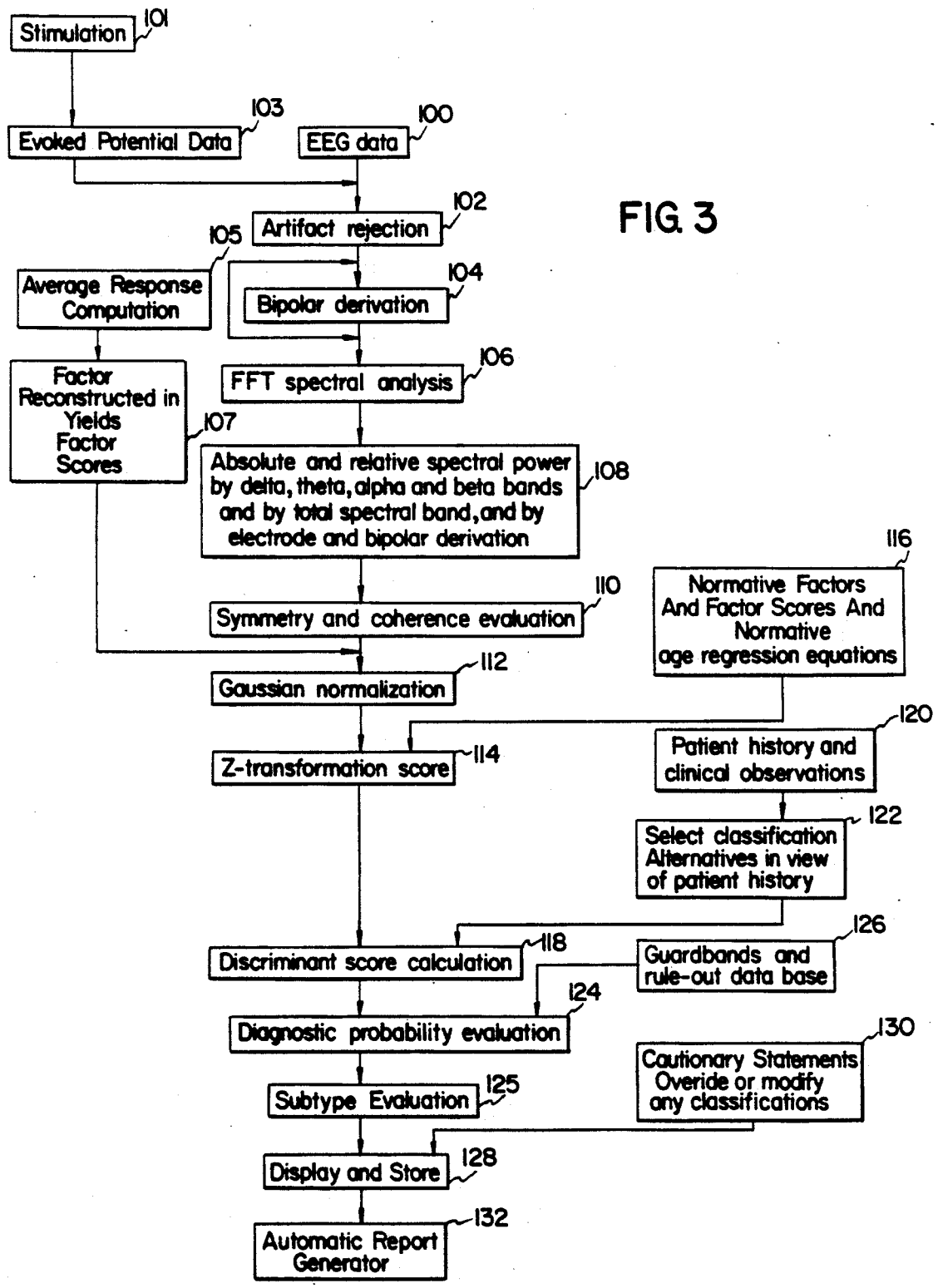
FIG. 3 is a flow chart illustrating main steps of a process of carrying out an example of the invented process.
Figure 4:
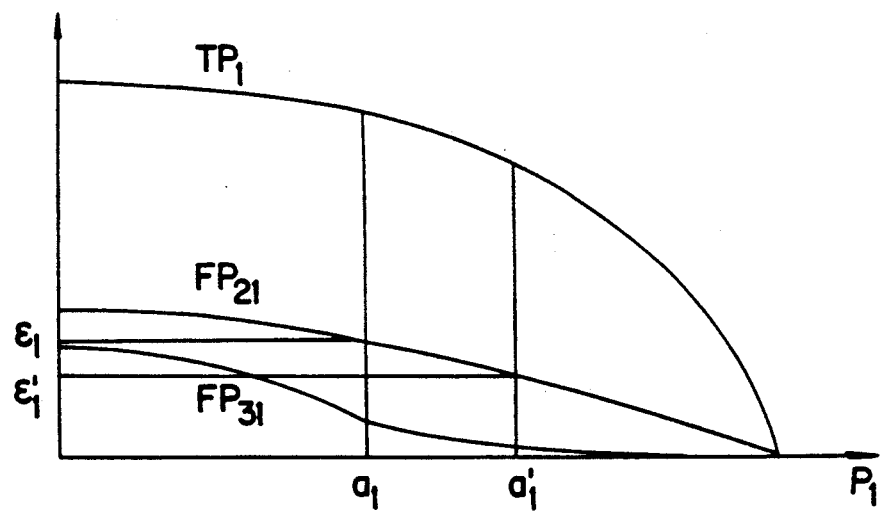
FIG. 4 illustrates classification curves for group 1 of a three-group discriminant.

Referring to FIG. 3, which is a flow chart illustrating main steps in carrying out an exemplary process in accordance with the invention, the relevant EEG data are provided at step 100, for example by using an instrument such as the Spectrum 32 instrument identified above. For EP data, step 101 generates appropriate stimuli applied to the patient and step 103 generate EP data, for example as currently done with said Spectrum 32 instrument. The EEG and/or EP data can be produced directly from electrodes placed on the scalp and other locations on the patient's body or they can be read from a storage device which archives previously derived EEG and EP data. Artifact rejection takes place at step 102, in the matter currently in use with instruments such as the Spectrum 32 device. This artifact rejection can be automatic, using the algorithmic process implemented by the Spectrum 32 instruments, or it can be totally manual, by visually evaluating the acceptability of a window of data and marking such data as an acceptable segment, or it can be an automatic artifact rejection process followed by manual confirmation or rejection of the automatically selected segments of data.

At step 104 the instrument derives any desired bipolar data by combining selected artifact-free segments of data from individual electrodes, and at step 106 the instrument starts further processing of the EEG data by applying thereto selected spectral analysis procedures, in this example by applying an FFT process to convert the time-varying amplitudes of the monopolar and bipolar signals to respective Fourier series expressed in terms of coefficients for respective frequencies. For EP data, the average response computation is carried out at step 105 and the results can be supplied to step 104, for bipolar signal derivation, and/or directly to step 106 for spectral analysis, as well as to step 107, for factor reconstruction as discussed above to derive factor Z-scores. At step 108 the instrument further processes the EEG and/or data, which now is in the frequency domain, by applying thereto further spectral analysis and statistical procedures to extract desired features, for example the absolute and relative spectral power by the traditional delta, theta, alpha and beta frequency bands and total spectral power of the EEG and/or EP data by monopolar and bipolar derivation. At step 110 further processing extracts symmetry and coherence features, for example in the manner currently followed in said Spectrum 32 instrument, and at step 112 Gaussian normalization is applied through known techniques to the extent needed that the relevant features of the EEG data from step 110 and/or the EP data from step 107 reasonably conform to a Gaussian distribution. The features extracted up to this point are in different dimensions and therefore cannot be conveniently combined for multivariate processing. In order to make further multivariate processing both convenient and meaningful, these features are Z-transformed at step 114 through the process currently practiced in said Spectrum 32 instrument, using for the purpose normative factors and factor Z-scores and normative age regression equations provided from step 116, to thereby generate for each feature a Z-score which is a finite number in units of probability.

These Z-scores are used in accordance with the invention at step 118 to calculate discriminant scores on the basis of selected features and/or factor scores in accordance with discriminant functions of the type set forth in the Tables above. The selection of these discriminant functions forms an important part of this invention but it should be clear that the functions illustrated in these Tables are only exemplary and the invention is not limited to those functions or to the diagnostic categories or the features and/or factors or the coefficients set forth in these tables.

In order to ensure greater reliability of the eventual classification, patient history and clinical observation data from step 120 can be used at step 122 for subjective or clinical decisions regarding a selection of classification alternatives in view of the patient history. For example, the entire classification process can be invalidated because a drug or some other condition is likely to make the results unreliable, or some of the classifications may be eliminated, or some classifications may be forced on the basis of a subjective evaluation rather than solely on the basis of the EEG data being processed. The discriminants generated at step 118 are supplied to step 124 which also receives information from step 126 regarding any applicable guardbands and rule-out levels of the type set forth in the Tables above and evaluates the diagnostic probabilities and carries out the diagnostic classifications in the manner discussed above. The resulting classifications are supplied to step 128 for display and storage, and any manual overrides or modification and cautionary statements are provided from step 130 to allow the operator to take into account any clinical observations or any patient history information relative to the classification of the individual in the relevant one or more diagnostic categories. If desired, a subtype evaluation can be carried out at step 125, using a similar form of a similarly derived discriminant function to classify an individual into a subgroup within a diagnostic category in which the individual is classified in step 124. At step 132 a report can be automatically generated and printed of the findings and evaluations and computations made in the preceding steps.

It should be noted that while the exemplary embodiment of the inventions has been described in detail above in terms of the processing of SP data, this is not a limitation of the invention and that the principles of the invention apply to similar processing of EP data as well to combinations of SP and EP data.

I claim:

1. A quantitative process of using brain electro-physiological data (BE) to classify an individual in one of more than two diagnostic categories comprising the machine-implemented steps of:
   providing BE data for a selected individual;
   processing said BE data by applying thereto selected spectral analysis and statistical procedures to extract a set of desired features of said BE data;
   deriving a respective discriminant score for each of a set of more than two diagnostic categories by selectively weighting and combining a number of selected ones of said features of said BE data;
   combining selected discriminant scores to derive respective probabilities that the individual belongs to selected diagnostic categories;
   applying selected guardbands or rule-out levels to said probabilities to enhance the reliability of classifying said individual into a diagnostic category on the basis of said probabilities; and
   classifying the individual into one of more than two diagnostic categories on the basis of said probabilities and said guardbands.

2. A quantitative process as in claim 1 in which said processing step comprises extracting said features in the form of age-corrected Z-scores which are in the same dimensional units.

3. A quantitative process as in claim 2 in which said processing step comprises ensuring a Gaussian distribution of the BE data from which said features are extracted.

4. A quantitative process as in claim 3 in which said processing step comprises extracting features which include absolute and relative spectral power of said BE data in selected frequency bands.

5. A quantitative BE process as in claim 4 in which said processing step comprises extracting features which include symmetry and coherence measures relating respective brain regions.

6. A quantitative process as in claim 5 in which said processing step comprises extracting said features for selected monopolar and bipolar derivations of said BE data.

7. A quantitative BE process as in claim 6 in which said deriving step comprises deriving said discriminant score for a selected diagnostic category by summing the products of said selected features with selected coefficients which typically differ as between both features and diagnostic categories.

8. A quantitative BE process as in claim 7 in which said combining step comprises dividing a discriminant score for a selected diagnostic category by a selected combination of the same discriminant score and the discriminant score for each remaining diagnostic category which is a part of the same set of at least two diagnostic categories to thereby derive a measure of the probability that the individual belongs to the selected diagnostic category rather than to another category in the same set of at least two categories.

9. A quantitative process as in claim 8 in which said combining step comprises deriving a discriminant score DS for a diagnostic category (i) in accordance with the expression $DS = (1/a)(A_1F_1 + A_2F_2 + \ldots + A_nF_n)$, where $(1/a)$ is a function coefficient and $A_1 - A_n$ are coefficients, $F_1 - F_n$ are selected features and n is an integer index.

10. A quantitative process as in claim 9 in which said step of applying selected guardbands comprises eliminating as unreliable those probabilities which permit more than a selected chance that an individual who belongs in a first category in said set of categories will be classified in another category in said set and said rule-out levels comprise threshold for eliminating as unreliable those probabilities which are below the threshold.

11. A quantitative process as in claim 10 in which said step of classifying the individual comprises displaying the classification.

12. A quantitative process as in claim 9 in which the step of deriving discriminant scores comprises deriving said discriminant scores in accordance with the features and coefficients of the following table for the diagnostic conditions stated therein:

| NORMAL vs PRIMARY DEPRESSION | | | |
|---|---|---|---|
| VARIABLE | NORMAL | PRIMARY | |
| $F_1$ Left Fronto/Temporal Bipolar Absolute Power | −0.03746 | 0.75010 | $A_1$ |
| $F_2$ Parietal Delta Bipolar Coherence | −0.02351 | −0.50883 | $A_2$ |
| $F_3$ Anterior Bipolar Coherence | −0.05034 | 1.05778 | $A_3$ |
| $F_4$ Central Bipolar Asymmetry | −0.02733 | 0.55487 | $A_4$ |
| $F_5$ Anterior Bipolar Asymmetry | −0 02111 | 0.81269 | $A_5$ |
| $F_6$ Anterior Beta Monopolar Relative Power | −0.10229 | 0.39695 | $A_6$ |
| Function Constant | −0.70165 | −2.89319 | FC |
| The guardbands for this case are: | | | |
| GUARDBANDS | a | a' | a" |
| Normal | 65 | 75 | 85 |
| Primary | 60 | 72 | 90 |

13. A quantitative process as in claim 9 in which the step of deriving discriminant scores comprises deriving said discriminant scores in accordance with the features and coefficients of the following table for the diagnostic conditions stated therein:

| NORMAL vs ABNORMAL for AGE GREATER THAN 50 YEARS | | |
|---|---|---|
| VARIABLE | NORMAL | ABNORMAL |
| All Regions Delta Bipolar Relative Power | 0.00000 | 0.00000 |
| All Regions Theta Bipolar Relative Power | −0.02961 | 0.36594 |
| All Regions Alpha | 0.05106 | −0.25480 |

-continued

| NORMAL vs ABNORMAL for AGE GREATER THAN 50 YEARS | | |
|---|---|---|
| Bipolar Relative Power All Regions Beta | 0.03480 | 0.31069 |
| Bipolar Relative Power Anterior All Frequencies | −0.02934 | 0.59480 |
| Bipolar Coherence Posterior All Frequencies | −0.00501 | 0.32559 |
| Bipolar Coherence Anterior All Frequencies | −0.01403 | 0.44775 |
| Bipolar Asymmetry Posterior All Frequencies | −0.02759 | 0.36308 |
| Bipolar Asymmetry Anterior Combined Frequencies | −0.05146 | 0.61554 |
| Monopolar Absolute Power Posterior Combined Frequencies | 0.00000 | 0.00000 |
| Monopolar Absolute Power Function Constant | −0.69861 | −2.23015 |

| GUARDBANDS | a | a' | a" |
|---|---|---|---|
| Normal | 65 | 75 | 80 |
| Abnormal | 80 | 85 | 90 |

-continued

| NORMAL vs ABNORMAL for AGE LESS THAN OR EQUAL TO 50 YEARS | | |
|---|---|---|
| Bipolar Asymmetry Posterior All Frequencies | −0.02686 | 0.38016 |
| Bipolar Asymmetry Anterior Combined Frequencies | −0.05588 | 0.53385 |
| Monopolar Absolute Power Posterior Combined Frequencies | 0.00000 | 0.00000 |
| Monopolar Absolute Power Function Constant | −0.69794 | −2.08874 |

| GUARDBANDS | a | a' | a" |
|---|---|---|---|
| Normal | 65 | 75 | 85 |
| Abnormal | 65 | 75 | 80 |

15. A quantitative process as in claim 9 in which the step of deriving disciminant scores comprises deriving said discriminant scores in accordance with the features and coefficients of the following table for the diagnostic conditions stated therein:

| NORMAL vs PRIMARY DEPRESSION vs DEMENTIA | | | |
|---|---|---|---|
| VARIABLE | NORMAL | PRIMARY | DEMENTIA |
| All Regions Theta Bipolar Relative Power | −0.02079 | 0.17234 | 1.30229 |
| Left Fronto/Temporal Bipolar Absolute Power | −0.04421 | 1.02014 | 0.04645 |
| Parietal Delta Bipolar Coherence | −0.00752 | −0.74484 | −0.27939 |
| Fronto/Temporal Delta Bipolar Coherence | −0.00899 | −0.53506 | 0.52687 |
| Anterior Bipolar Coherence | −0.04753 | 0.77702 | 0.94400 |
| Central Bipolar Asymmetry | −0.03740 | 0.57220 | 0.62493 |
| Anterior Bipolar Asymmetry | −0.01438 | 0.64457 | 0.43654 |
| Cz Theta Monopolar Relative Power | −0.00180 | −0.79164 | 1.09048 |
| P3 Alpha Monopolar Relative Power | −0.24440 | 2.82880 | 1.73974 |
| O1 Alpha Monopolar Relative Power | 0.27980 | −4.06245 | −1.92960 |
| Anterior Beta Monopolar Relative Power | −0.08958 | 0.35577 | 0.59821 |
| Function Constant | −1.11186 | −4.39809 | −4.63901 |

| GUARDBANDS | a | a' | a" |
|---|---|---|---|
| Normal | 42 | 80 | 90 |
| Primary | 40 | 70 | 75 |
| Dementia | 45 | 75 | 95 |

14. A quantitative process as in claim 9 in which the step of deriving disciminant scores comprises deriving said discriminant scores in accordance with the features and coefficients of the following table for the diagnostic conditions stated therein:

| NORMAL vs ABNORMAL for AGE LESS THAN OR EQUAL TO 50 YEARS | | |
|---|---|---|
| VARIABLE | NORMAL | ABNORMAL |
| All Regions Delta Bipolar Relative Power | 0.00000 | 0.00000 |
| All Regions Theta Bipolar Relative Power | 0.00000 | 0.00000 |
| All Regions Alpha Bipolar Relative Power | 0.04777 | −0.48710 |
| All Regions Beta Bipolar Relative Power | 0.02004 | 0.46486 |
| Anterior All Frequencies Bipolar Coherence | −0.02881 | 0.75448 |
| Posterior All Frequencies Bipolar Coherence | −0.00612 | 0.30889 |
| Anterior All Frequencies | −0.01651 | 0.48136 |

16. A quantitative process as in claim 9 in which the step of deriving disciminant scores comprises deriving said discriminant scores in accordance with the features and coefficients of the following table for the diagnostic conditions stated therein:

| UNIPOLAR vs BIPOLAR DEPRESSION | | |
|---|---|---|
| VARIABLE | UNIPOLAR | BIPOLAR |
| Right Temporal Beta Bipolar Relative Power | −0.91564 | 1.26876 |
| Left Lateral Alpha Monopolar Relative Power | −0.15510 | 1.53144 |
| O1 Delta Monopolar Asymmetry | −0.13401 | 0.13963 |
| Right Temporal Alpha Bipolar Relative Power | −0.72519 | 1.57794 |
| Left Temporal Alpha Bipolar Relative Power | −0.06270 | −1.59622 |
| Beta C3 Monopolar Relative Power | 0.04106 | −1.97474 |
| Beta Cz Monopolar Relative Power | 0.26946 | 1.57156 |
| Fronto-temporal Bipolar Absolute Power Asymmetry | 0.01198 | −0.75104 |
| Function Constant | −0.89218 | −2.09228 |

| GUARDBANDS | a | a' | a" |
|---|---|---|---|

-continued

| UNIPOLAR vs BIPOLAR DEPRESSION | | | |
|---|---|---|---|
| Unipolar | 50 | 77 | 92 |
| Bipolar | 55 | 82 | 87 |

17. A quantitative process as in claim 9 in which the step of deriving disciminant scores comprises deriving said discriminant scores in accordance with the features and coefficients of the following table for the diagnostic conditions stated therein:

| PRIMARY DEPRESSION vs ALCOHOL ABUSE | | |
|---|---|---|
| VARIABLE | PRIMARY | ALCOHOLC |
| Left Central Beta Bipolar Relative Power | −0.07380 | 0.58635 |
| Left Fronto/Temporal Beta Bipolar Relative Power | −0.08163 | 0.58543 |
| Right Fronto/Temporal Bipolar Absolute Power | 0.76931 | −0.20846 |
| Fronto/Temporal Delta Bipolar Coherence | −0.80124 | −0.05935 |
| Fronto/Temporal Beta Bipolar Coherence | −0.26573 | 0.60565 |
| Posterior Beta Bipolar Asymmetry | 0.45822 | −0.59687 |
| Fz Theta Monopolar Relative Power | −0.07747 | −0.96582 |
| Constant | −1.79117 | −2.61208 |
| RULE-OUT LEVEL: | | |
| Alcoholic | 65 (if $P_i \geq 65\%$, rule out alcoholism) | |

18. A quantitative process as in claim 9 in which the step of deriving disciminant scores comprises deriving said discriminant scores in accordance with the features and coefficients of the following table for the diagnostic conditions stated therein:

| BIPOLAR DEPRESSION vs ALCOHOL ABUSE | | |
|---|---|---|
| VARIABLE | BIPOLAR | ALCOHOLC |
| Right Parietal/Occipital Beta Bipolar Relative Power | 0.58452 | 0.08115 |
| Parietal/Occipital Delta Bipolar Coherence | −0.72523 | −0.20808 |
| Fronto/Temporal Delta Bipolar Coherence | −0.95221 | 0.20967 |
| Parietal/Occipital Beta Bipolar Coherence | −0.01620 | 0.45588 |
| Posterior Bipolar Asymmetry | 0.65121 | −0.80888 |
| Posterior Alpha Monopolar Relative Power | 0.83039 | −0.51708 |
| Fz Theta Monopolar Absolute Power | 1.02508 | −1.29232 |
| Constant | −2.16285 | −1.88824 |
| RULE-OUT LEVEL: | | |
| Alcoholic | 51 | |

19. A quantitative process as in claim 9 in which the step of deriving disciminant scores comprises deriving said discriminant scores in accordance with the features and coefficients of the following table for the diagnostic conditions stated therein:

| ELDERLY DEMENTIA vs ALCOHOL ABUSE | | |
|---|---|---|
| VARIABLE | DEMENTIA | ALCOHOLC |
| Left Central Theta Bipolar Relative Power | −0.03469 | 0.91110 |
| Right Central Theta Bipolar Relative Power | 1.06487 | −1.18625 |
| Left Central Beta Bipolar Relative Power | 0.03015 | 0.89450 |
| Parietal/Occipital Beta Bipolar Coherence | −0.08565 | 0.89726 |
| C3-C4 Theta Monopolar Asymmetry | −0.40997 | 0.09382 |
| Constant | −1.82594 | −1.98809 |
| RULE-OUT LEVEL: | | |
| Alcoholic | 51 | |

20. A quantitative process as in claim 9 in which the step of deriving disciminant scores comprises deriving said discriminant scores in accordance with the features and coefficients of the following table for the diagnostic conditions stated therein:

| UNIPOLAR DEPRESSION vs ALCOHOL ABUSE | | |
|---|---|---|
| VARIABLE | UNIPOLAR | ALCOHOLC |
| Left Central Beta Bipolar Relative Power | −0.12390 | 0.86921 |
| Left Fronto/Temporal Beta Bipolar Relative Power | −0.31110 | 0.86605 |
| Fronto/Temporal Delta Bipolar Coherence | −0.59866 | −0.14523 |
| Left Central Bipolar Absolute Power | 0.88585 | −0.14734 |
| Parietal/Occipital Beta Bipolar Coherence | 0.00458 | 0.90921 |
| Posterior Bipolar Asymmetry | 0.50132 | −0.57529 |
| Constant | −1.71888 | −2.47368 |
| RULE-OUT LEVEL: | | |
| Alcoholic | 51 | |

21. A quantitative EEG method comprising:
deriving quantitative EEG data for an individual and subjecting said EEG data to preprocessing including artifact rejection to reduce said EEG data from artifact-free segments, subjecting said artifact-free segments to spectral processing to extract desired features thereof, applying transforms to said features as needed to ensure Gaussianity and Z-transforming said features on the basis of normative age regression data for a population of individuals assumed to be normal to thereby derive Z-scores for selected features and any desired combinations of features; and
deriving discriminant scores for selected diagnostic categories from Z-scores derived from an individual's EEG data by combining for each respective discriminant function selected ones of the individual's Z-scores weighted by selected coefficients specific to the respective diagnostic category, combining selected discriminant scores to evaluate the probability that the individual belongs to a particular one of two or more selected diagnostic categories and applying guardbands to the evaluated probabilities to ascertain the level of confidence that the probability correctly classifies the individual into a diagnostic category.

* * * * *